United States Patent [19]
Wallace et al.

[11] 4,256,461
[45] Mar. 17, 1981

[54] METHOD AND APPARATUS FOR EQUILIBRATING GAS AND LIQUID IN A TRANSPORTABLE VESSEL—SYRINGE TONOMETER

[76] Inventors: William D. Wallace, 1550 S. 1300 East, Salt Lake City, Utah 84105; Christopher A. Cutler, 649 E. 1130 North, Bountiful, Utah 84010; Justin S. Clark, 720 E. 3120 South, Salt Lake City, Utah 84106; Frederick L. Farr, 2834 E. 2100 South, Salt Lake City, Utah 84109

[21] Appl. No.: 39,776

[22] Filed: May 17, 1979

[51] Int. Cl.³ .................. G01N 33/96; G01N 33/50
[52] U.S. Cl. ........................... 23/230 B; 23/928; 261/82; 261/122; 422/50; 422/99
[58] Field of Search ............... 23/230 B, 928; 422/68, 422/102, 99, 101, 50; 55/68; 261/122, 82, 112; 210/359

[56] References Cited
U.S. PATENT DOCUMENTS

| | | | |
|---|---|---|---|
| 3,127,254 | 3/1964 | Astrup et al. | 261/112 X |
| 3,642,260 | 2/1972 | Danjes et al. | 261/122 |
| 3,870,639 | 3/1975 | Moore et al. | 422/101 X |
| 3,973,915 | 8/1976 | Raffaele et al. | 23/230 B |
| 3,977,606 | 8/1976 | Wyss | 261/122 |
| 4,057,499 | 11/1977 | Buono | 210/359 X |
| 4,060,486 | 11/1977 | Schreiber | 261/122 |

OTHER PUBLICATIONS
Noonan et al., Clinical Chemistry, vol. 20, No. 6, 1974, pp. 660–665.

*Primary Examiner*—R. E. Serwin
*Attorney, Agent, or Firm*—H. Ross Workman; Rick D. Nydegger; J. Winslow Young

[57] ABSTRACT

Method and apparatus for gas-liquid equilibration (tonometry) in a transportable vessel. Specifically the method and device is concerned with tonometry of blood or buffer solution in a syringe. The compartment formed when a syringe plunger is partially inserted into a syringe barrel serves as a tonometer chamber where gas of known composition is bubbled through a liquid sample. Gas enters the chamber through small holes in the tip of the syringe plunger and bubbles upward through the sample. The syringe plunger itself is a second chamber which is used for heating and humidifying the gas prior to entering the tonometer chamber. The entire syringe is housed in a temperature controlled environment during equilibration. This environment allows observation of the entire tonometry process. After equilibration the syringe tonometer is easily removed from the heat controlled environment and is used as the sample's transport vessel. The syringe configuration allows easy entry of the sample into the target sytem, e.g. a blood gas analyzer.

17 Claims, 8 Drawing Figures

METHOD AND APPARATUS FOR EQUILIBRATING GAS AND LIQUID IN A TRANSPORTABLE VESSEL—SYRINGE TONOMETER

BACKGROUND OF THE INVENTION

1. Field of the Invention

The invention relates to the methods and apparatus for equilibrating an aqueous solution such as buffer liquid or blood with gas. Particularly the invention is concerned with an apparatus and process for equilibrating solutions for preparation of standards useful in quality control of laboratory instrumentation. For example, quality control for blood gas analyses in the clinical laboratory comprises both calibration of the blood gas analyzer as well as reference controls for the analyzer. The invention provides these controls for one- and two-point calibrations and also provides tonometered samples for reference control. In addition, the invention can be used for blood $P_{50}$ oxyhemoglobin-dissociation curve determination and for other laboratory instrumentation calibration. A simple, fast and error-free tonometry system has great practical application in the clinical and research laboratory.

2. Prior Art

There is an increasing widespread use of blood gas analyzers in clinical laboratories. The electrode sensors which measure $PO_2$, $PCO_2$ and pH in these analyzers have inherent problems maintaining accuracy and reliability. This has accelerated the need for methods to assure quality control of these devices. Tonometry (the equilibration of gas partial pressures between liquid and gas) is considered to be the preferred method in providing the standards to be used for both calibration and reference controls. Simple as the problem of tonometering an aqueous solution (e.g. blood) with a known gas mixture may appear at first, it is often difficult to accomplish because of several conditions which have to be met. The ideal tonometer should have the following characteristics: (1) it should equilibrate the partial pressures of gases in an adequate quantity of sample with a minimal volume of known gas composition while maintaining the pressure at the gas-liquid interface at a known level; (2) the equilibration should occur at a known and controlled temperature, at a rapid rate, and without dehydration (or hemolysis to blood); (3) transfer of the sample to the analyzing chamber must be such as to avoid any deteriorating air contamination and such transport should be accomplished rapidly and easily; and (4) the tonometer should be simple to use, easy to clean and maintain, compact, and cost effective. The conditions of adequate gas-liquid equilibration, temperature control, and gas humidification have been achieved by many of the present instruments. However, the problem of transport of the tonometered sample to the analyzer has not been solved.

There are four general tonometer concepts which have been developed. Perhaps the most widely used method to date is the thin film approach. The instrument used with this method operates by introducing a known gas composition over the surface of the liquid in a swirling or rotating flask so that a large surface area of the liquid is placed in contact with the gas. This method generally requires twenty to thirty minutes and present instruments prepare only one sample at a time. This concept is not entirely satisfactory since the sample may be altered as it is transferred to a transport vessel.

A second method gaining much popularity today allows analyzed gas to bubble through the liquid sample to achieve a gas-liquid equilibration. The tonometer used with this process is inherently the simplest and cheapest type available. Instruments used with this approach employ multiple chambers for up to three separate simultaneous sample preparations. With this bubble method it is assumed that the gas-liquid interface pressure is at ambient level and this assumption may not be correct. A pressure difference is caused by (1) the increased hydrostatic pressure inside the bubble which is located below the liquid sample surface, and (2) the increased pressure inside the bubble due to surface tension when the bubble diameters are very small.

The problem of sample transportation has not been effectively solved since current bubble tonometers require an intermediate transport vessel for delivery of the sample to the analyzer. Air contamination is a possibility whenever the sample is transferred to an intermediate chamber between the location of tonometry and the location where the sample is analyzed.

Another tonometer design which is losing popularity uses oscillation or vibration of the sample within a temperature-controlled bath while a gas stream of known concentration passes over the surface. A fourth design makes use of highly gas permeable, liquid impermeable membranes or tubes to equilibrate a gas placed on one side of the membrane with the liquid on the other. Presently, there are no practical membrane tonometers available. The last two described designs have the same transport problems as the others previously described.

BRIEF DESCRIPTION OF THE INVENTION

The principal object of the invention is to provide a tonometry system wherein sample standards can be prepared rapidly and conveniently and which will yield measurements that are more reliable and accurate than those obtained with the prior art. A more specific object is to provide method and apparatus for transporting the tonometered sample, without contamination, to the site of use. Another object is to provide an accurate temperature control of the sample during the tonometry and convenient observation of the equilibration process. A further object of the invention is to minimize the cleaning and maintenance such that the system is extremely practical to use.

These and other objects are realized in a method and apparatus for gas-liquid equilibration employing a single two compartment vessel to serve as (1) a tonometry chamber, (2) a humidifying chamber, and (3) a transport and delivery syringe movable to the analyzing device. The vessel's tonometry chamber is formed by partially inserting a syringe plunger into a syringe barrel. The aqueous sample is placed in this chamber. Gas of known composition from either a premixed gas cylinder or from an on-site gas mixing system, such as MEDICOR'S patented Precision Gas Mixer, shown by U.S. Pat. No. 4,062,373 is bubbled upward through the sample. Gas enters the tonometry chamber through small holes in the tip of the syringe plunger. These holes are punched in a shaped elastic membrane such that they open under pressure going into the tonometry chamber but open only under a high pressure coming back. This allows gas to enter the chamber freely but prevents back leakage of the aqueous sample during tonometry and ultimate expulsion at the site of use. The syringe plunger itself constitutes a second chamber which is used for heating and humidifying the gas prior to entering the tonometry chamber. The lower portion of the syringe plunger contains water. The base of the plunger is closed off with another punched elastic membrane with properties similar to the one forming its tip. Thus, gas from a low pressure source enters the humidifying chamber through the base membrane, bubbles up through the water, enters the tonometry chamber through the plunger tip membrane, bubbles up through the sample, and vents to atmosphere through the syringe tip. The bubble size and hydrostatic height are controlled to maximize equilibration efficiency and minimize bubble-atmospheric pressure differences. The entire vessel is in thermal contact with a temperature-controlled environment and is conveniently visable to the user through a small door during the entire tonometry period. After temperature and pressure equilibration has occurred, the syringe tonometer can be removed from the heat source, disconnected from the gas source, and transported to the blood-gas analyzer or the like for use. The sample is then expelled from the vessel by familiar syringe-plunger action into the analyzer.

The above-described features allow for distinct advantages of the present invention over prior art systems for assurance of accurate and precise analyzer calibration and quality reference control. The system equilibrates the partial pressures of gases in a selectable, adequate sample size, rapidly, with a minimal gas volume, at a controlled temperature, and without dehydration. A salient advantage of the system is the unique transportable equilibration vessel design which avoids deteriorating sample contamination. Thus, the system has been designed to minimize sample handling errors caused by the technician. Finally, the system is practical since it is compact, simple to use, easy to clean and maintain and is cost effective.

These and other objects, features and advantages will be more apparent to those skilled in the art after a detailed study of the specification hereinafter with reference to the attached drawings.

THE DRAWINGS

In the drawings:

FIG. 1 is a schematic diagram of the preferred embodiment of the gas tonometry system of the present invention in which gas is bubbled through two liquid chambers, both of which are contained in a single temperature-controlled syringe;

FIG. 2, an enlarged and more detailed side elevation view of the tonometer of the present invention;

FIG. 3a, a cross-sectional exploded view of the plunger ends of the tonometer with the bubble channels closed;

FIG. 3b, a top plan view of the same plunger ends showing the pattern of the bubble channels;

FIG. 4, a perspective view of a two tonometer configuration of the preferred embodiment of metal heating block with the door open for clarity;

FIG. 5, a top plan view of the heating block of FIG. 4, with the door closed;

FIG. 6, a front elevation view of the block as shown in FIG. 4; and

FIG. 7, a side elevation view of the block as shown in FIG. 4.

DETAILED DESCRIPTION OF THE INVENTION

Figure 1:
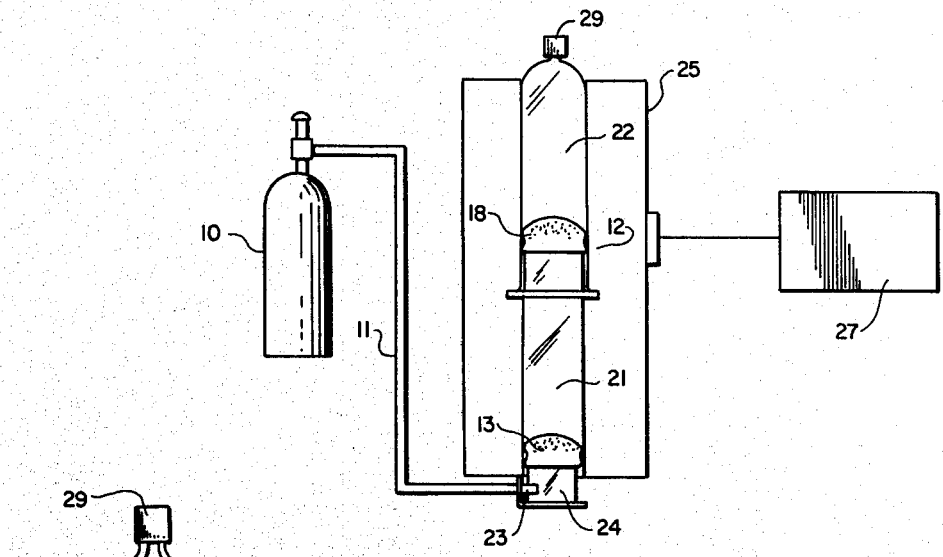
Figure 2:
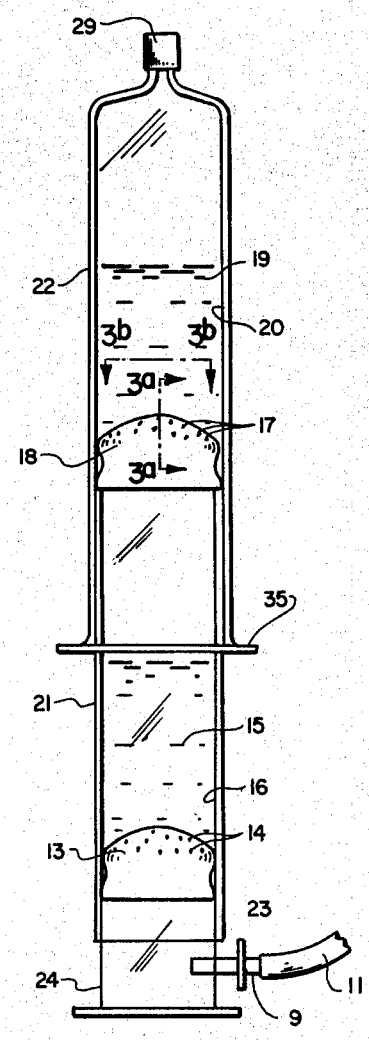

The preferred embodiment of the invention is represented schematically in FIG. 1 with the tonometer details being shown in FIG. 2. Gas from a regulated pressure source 10 flows through a line 11 to the tonometer, shown generally at 12, at an adjustable rate. Upon initiation of flow, a pressure is built at the concave side of a flexible humidifier plunger base membrane 13 in order to open channels 14 through the base membrane to gas flow. Gas then bubbles up through water 15 with which the humidifying chamber 16 is partially filled. As the pressure in the hymidifying chamber builds up on the concave side, it opens channels 17 in a plunger tip membrane 18 at one end of a tonometer chamber 20. Both the humidifier plunger base membrane 13 and tonometer plunger tip membrane 18 are made as caps of a suitable elastic type material, such as for example, polyvinyl chloride. The channels 14 and 17 are made such that an initial low forward pressure of typically one to two psig is required to open them, but they will not open to reverse flow unless greater pressures, i.e. three to four psig are reached. Thus, the membranes effectively function as one-way check valves. Channels 14 and 17 are punched through the elastic membranes with needles (not shown) and the sizes of the orifices formed is dependent on the material from which the membranes are made and the thickness of the materials. Because of the curved gap configuration a lower pressure differential across the membranes than about three to four psig, with the high pressure at the convex side of the membranes, will collapse the membranes to close the passages. When a higher differential pressure, i.e. three to four psig is reached on the convex side the passages will again open. However, since the higher differential pressures are not usually reached the shaped membranes effectively act as check valves.

As the gas leaves the channels 17 in the tonometer plunger tip membrane 18, it forms small bubbles about 1 mm in diameter which subsequently rise through liquid 19 in the tonometer chamber 20 to achieve gas-liquid equilibration. The small bubbles maximize the liquid volume to gas surface area ratio, thereby decreasing equilibration time.

Central to the invention is the fact that the humidifying chamber 16 is formed by the hollow plunger barrel 21 of an ordinary glass syringe while at the same time the tonometer chamber 20 is located in the usual glass syringe barrel 22. Thus, after detaching the connector 23 and its attached inlet line 11 from a closed end of tube 24 to which the other end of plunger base membrane 13 is mounted, the tonometer is transportable to a location where the tonometered sample will ultimately be used. For proper equilibration, the tonometer 12, comprising both the humidifying chamber 16 and the actual tonometer chamber 20 must be accurately maintained at the desired temperature. This is accomplished by fitting the whole tonometer into a metal block 25, or the like, and then controlling the temperature of the metal block with a temperature controller 27. The present invention uses a simple electronic feedback control system to maintain the temperature in the syringe to within ±0.1° C. Such temperature control systems are well known and a commercially available and therefore the system is not described in detail herein. While the tonometer is here described as fitting into a metal block with temperature control of the block being maintained to regulate the temperature of the inserted tonometer it will be apparent that the tonometer could be inserted in other mediums, such as water, which can be temperature controlled.

As best seen in FIG. 2, connector 23 receives incoming gas from line 11 and is frictionally secured in the wall of and opens into a small chamber 26 formed by the tube 24 which is fixed in plunger barrel 21 directly upstream of the humidifier plunger base membrane 13.

As the gas passes through the channels 14 of the plunger base membrane 13, it forms bubbles and rises to the top of the humidifying chamber 16. Chamber 16 typically has a volume of 10 ml, half of which is occupied by water 15. This results in a relatively small dead space above the water which assures fast gas washout while simultaneously accomplishing complete temperature equilibration and water vapor equilibration of the gas before it passes into the tonometer chamber 20. The humidifying chamber 16 may be made of propionate plastic or a similar molded material, for example.

The volume of the tonometer chamber 19 is typically 20 ml. When an aqueous buffer solution is used half of the tonometer chamber can be filled with the solution. When using whole blood, a slightly smaller blood sample can be tonometered at one time.

After an appropriate equilibration time, connector 23 and the attached gas input line 11 are disconnected from the tonometer. The tonometer can now be removed from the temperature-controlled environment provided by block 25. The excess gas must be expelled from above the equilibrated liquid within a short time period (30 seconds, for example) and this is accomplished by telescoping the plunger barrel 21 more fully into barrel 22. With the excess gas discharged from barrel 22 additional gas is not available to enter the equilibrated liquid as the liquid cools. The small discharge opening from the barrel 22 does not permit any significant contamination of the tonometered liquid, but, if desired, a cap (not shown) can be placed over the discharge tip.

A conventional Luer lock tip 29 at the discharge end of barrel 22 is preferably used so that the tonometer may be readily attached to commonly available laboratory apparatus and devices.

Figure 3A:
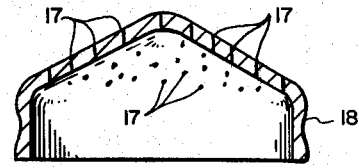
Figure 3B:
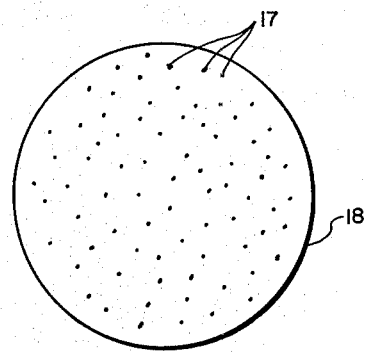
Figure 5:
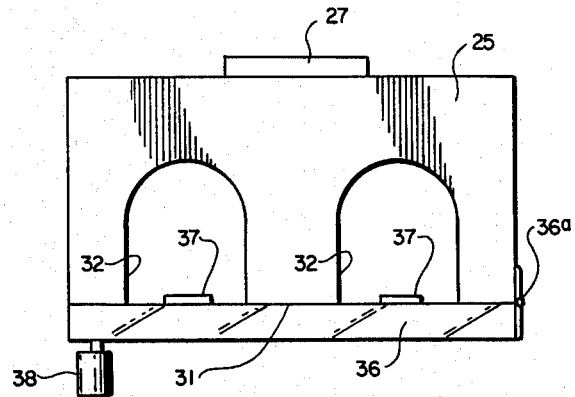

A typical cross-sectional view of the plunger ends, i.e. plunger base membrane 13 and plunger tip membrane 18, is shown in FIG. 3a, where the plunger base membrane 13 is illustrated with the gas channels in their closed condition. A top view (FIG. 3b) shows a typical orientation pattern of the channels in the membrane ends. The plunger membranes, comprising base membrane 13 and tip membrane 18, are sealed to their respective bodies (base 13 to tube 24 and tip 18 to barrel 21) with an epoxy glue.

Figure 4:
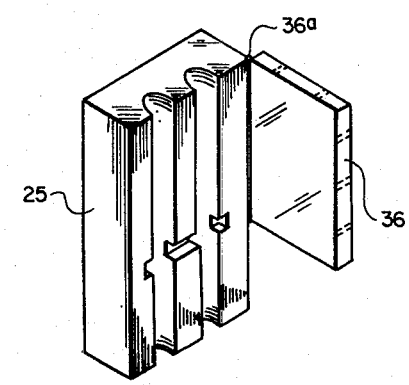
Figure 6:
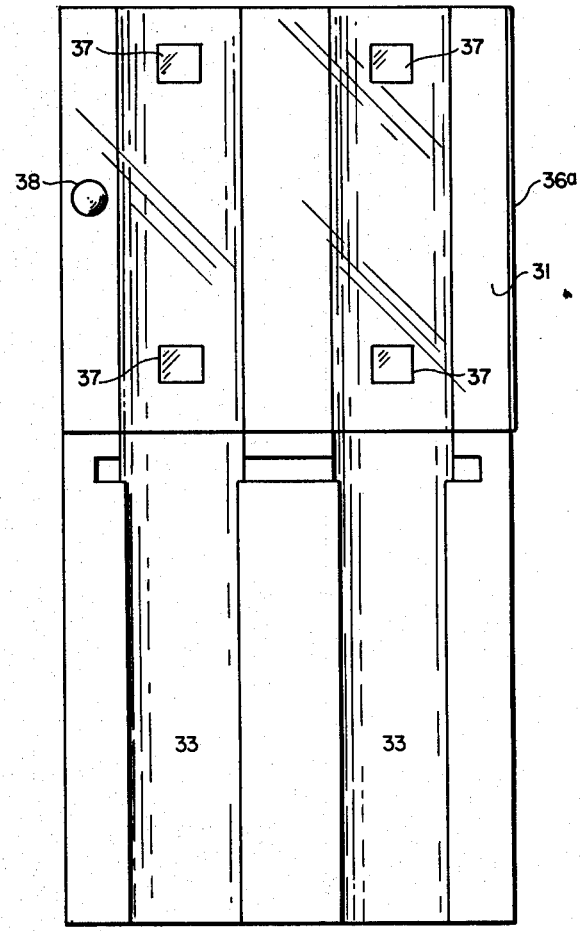
Figure 7:
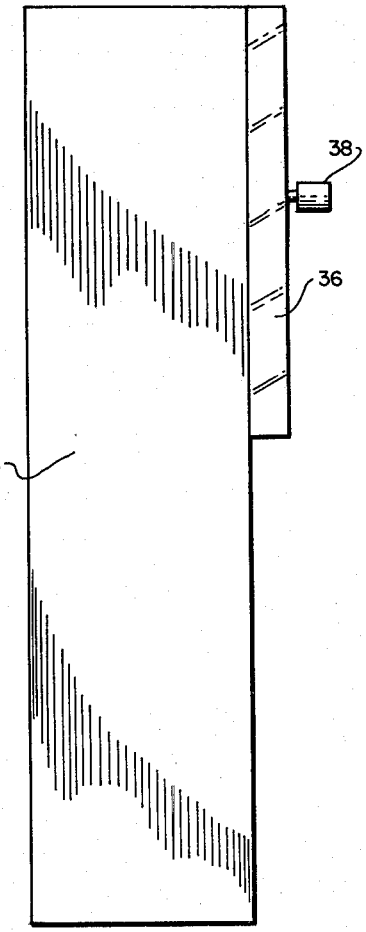

The preferred embodiment of the temperature-control system includes the metal block 25, FIG. 4, into which syringe tonometer 12 closely fits. A top portion of one face 31 of the block includes grooves 32 having the same dimensions as the outside diameter of the plunger barrel 22. Grooves 33 in the lower half of the face 31 of block 25 aligned with grooves 32 and are reduced in diameter to correspond to the outside diameter of the plunger barrel 22. A transverse slot 34 at the junctions of grooves 32 and 33 accommodates the usual flanges 35 of the syringe barrel 22. A door 36, preferably made of a transparent acrylic plastic, is connected by a hinge 36a to the block 25 to close over the face 31. Pads of urethane foam 37 on the door serve as cushions and protect the glass components of the tonometers as the door is closed while holding the tonometers securely in place so that good heat transfer can be obtained. The transparent door 36 allows viewing of the liquid being tonometered. A syringe tonometer 12, as seen in FIG. 2, is easily inserted into and removed from the metal block assembly of FIG. 4, and as shown, two such tonometers can be inserted at once. Obviously the temperature control system can be set up to simultaneously receive any desired number of tonometers. In the preferred embodiment, a commercially available, known, combination heater-sensor pad 27 is attached to the back of the block 30 to precisely control the temperature of the system. A knob 38 on the door permits it to be easily opened.

The typical sequence of events in the use of the present equilibration system is as follows: (1) 5 ml of water is placed in the plunger barrel 21 (humidifying chamber 16) and the plunger barrel is inserted into the syringe barrel 22; (2) the tonometer chamber 20 is filled with the desired amount of buffer or blood liquid 19 (maximum volumes are approximately 10 ml and useful minimum volumes are 1 ml); (3) the tonometer 12 is placed in position in the temperature-controlled block 25 (which is pre-heated to the desired temperature); (4) the input gas line 11 is attached by its connector 23 to tube 24; (5) the gas is flowed through line 11, connector 23 and tube 24 and is allowed to bubble through the liquid 15 for a time period which typically may be ten minutes (although in the present invention, temperature equilibration is usually achieved in five minutes and complete gas partial pressure equilibration in the case of maximal fluid volume is achieved in less than ten minutes total time); (6) connector 23 and the gas input source line 11 is disconnected from the tube 24 so that the syringe plunger can be freely telescoped in the syringe barrel; (7) the tonometer is removed from the temperature-controlled block 25; and (8) excess gas not required for equilibration is ejected from the tonometer by telescoping the syringe plunger into the syringe barrel. At this point the equilibrated liquid is ready for use.

As previously noted, the present invention also envisions enlargement of the system to situations in which multiple samples can be equilibrated simultaneously using multiple tonometers and multiple gas inputs in a single, appropriately constructed, temperature-controlled block.

The present invention provides a tonometering method and apparatus wherein a liquid may be tonometered in a vessel and then be transported in the same vessel under conditions providing for substantially anaerobic delivery to a point of use.

While the invention has been described in connectin with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits to the appended claims.

We claim:

1. An apparatus for equilibrating gas and liquid, said apparatus comprising:
 a first chamber adapted to be at least partially filled with a humidifying liquid, said first chamber having a fitting for connection to a pressurized source of gas;

a second chamber slidably mounted in relation to said first chamber, said second chamber being adapted to be at least partially filled with a liquid sample to be tonometered and having a fluid discharge port for expulsion of the fluids contained in said second chamber; and one-way valve means positioned between said first and second chambers, said valve means permitting one-way flow of pressurized gas from said first chamber to said second chamber.

2. The apparatus of claim 1 wherein said second chamber is formed by the outer barrel of a syringe and wherein said first chamber is formed inside the plunger of said syringe.

3. The apparatus of claim 1 wherein said one-way valve means comprise a membrane having fluid passageways formed therethrough, said membrane being constructed from elastomeric material and having a concave-convex shape designed to close said passageways in order to prevent reverse flow of fluids from said second chamber to said first chamber.

4. The apparatus of claim 1 wherein said first chamber further comprises a one-way valve means positioned at said fitting so as to permit flow of pressurized gas from said source of gas to said first chamber.

5. The apparatus of claim 1 further comprising means for maintaining thermal equilibrium between said first and second chambers.

6. The apparatus of claim 5 wherein said means for maintaining thermal equilibrium comprise a heat-conductive block which surrounds at least a portion of both of said chambers.

7. The apparatus of claim 6 wherein said block comprises means for securely locking said chambers within the block.

8. The apparatus of claim 7 wherein said locking means comprise a transparent door through which the tonometered liquid sample in said second chamber may be visually inspected.

9. The apparatus of claim 5 wherein said means for maintaining thermal equilibrium further comprise a temperature control device for keeping the temperature of said chambers at an essentially constant temperature.

10. A syringe tonometer for equilibrating the partial pressures in a liquid sample with a gas of known composition, such that the equilibrated liquid sample may be readily transported and discharged into an analyzing chamber without any substantial risk of deteriorating air contamination, the syringe tonometer comprising:

a plunger having a first chamber formed inside the barrel of said plunger, said first chamber being adapted to be at least partially filled with a humidifying liquid and having a fitting for connection to a pressurized gas source;

an outer syringe barrel for slidably receiving one end of said plunger in fluid-tight engagement, the inside of said outer syringe barrel forming a second chamber adapted to be at least partially filled with a liquid sample to be tonometered and having a fluid discharge port at one end thereof; and one-way valve means positioned between said first and second chambers, said valve means permitting one-way flow of pressurized gas from said first chamber to said second chamber.

11. The apparatus of claim 10 wherein said one-way valve means comprise a membrane having fluid passageways formed therethrough, said membrane being constructed from elastomeric material and having a concave-convex shape designed to close said passageways in order to prevent reverse flow of fluids from said second chamber to said first chamber.

12. The apparatus of claim 11 wherein said first chamber further comprises a one-way valve means positioned at said fitting so as to permit flow of pressurized gas from said gas source to said first chamber.

13. The apparatus of claim 12 further comprising a heat-conductive block which surrounds at least a portion of both of said chambers so as to maintain thermal equilibrium therebetween.

14. The apparatus of claim 13 wherein said block comprises a transparent door for securely locking said syringe tonometer within the block while still permitting visual inspection of said second chamber through the transparent door.

15. The apparatus of claim 14 further comprising a temperature control device for maintaining the temperature of said chamber at an essentially constant temperature.

16. A syringe tonometer for equilibrating the partial pressures in a liquid sample with a gas of known composition, such that the equilibrated liquid sample may be readily transported and discharged into an analyzing chamber without any substantial risk of deteriorating air contamination, the syringe tonometer comprising in combination:

a plunger having a first chamber formed inside the barrel of said plunger, said first chamber being adapted to be at least partially filled with a humidifying liquid and having a fitting for connection to a pressurized gas source;

an outer syringe barrel for slidably receiving one end of said plunger in fluid-tight engagement, the inside of said outer syringe barrel forming a second chamber adapted to be at least partially filled with a liquid sample to be tonometered and having a fluid discharge port at one end thereof;

a first concave-convex shaped elastomeric membrane placed at one end of said first chamber, said first membrane having needle passageways formed therethrough such that one-way flow of pressurized gas from said first chamber to said second chamber may be accomplished;

a second concave-convex shaped elastomeric membrane placed at the other end of said first chamber, said second membrane having needle passages formed therethrough for permitting one-way flow of pressurized gas from said gas source to said first chamber;

a heat-conductive block having channels formed therein for receiving said syringe tonometer such that the heat-conductive block will surround at least a portion of both of said chambers;

a transparent door for securely locking said syringe tonometer inside said heat-conductive block while permitting visual inspection of said second chamber through said transparent door; and a temperature control device for controlling the temperature of said heat-conductive block such that the temperature of said chambers may be maintained at an essentially constant value.

17. A method of equilibrating the partial pressures in a liquid sample with a gas of known composition such that the equilibrated liquid sample may be readily transported and discharged into an analyzing chamber without any substantial risk of deteriorating air contamination, the method comprising the steps of deteriorating air contamination, the method comprising the steps of:
- partially filling a first chamber formed inside the barrel of a syringe plunger with a humidifying liquid;
- placing said liquid sample inside a second chamber formed inside the outer barrel of said syringe;
- placing said syringe into a heat-conductive block such that the block will surround at least a portion of both of said chambers;
- connecting said first chamber to a pressurized gas source;
- heating said block so as to maintain the temperature of both the chambers at an essentially constant value;
- bubbling said gas through said humidifying liquid and through said liquid sample so as to achieve equilibration of said liquid sample;
- removing said syringe from the heat-conductive block;
- pushing said syringe plunger further into the outer barrel of said syringe so as to eject the remaining gas from said second chamber and thereafter transporting the syringe to an analyzing chamber; and
- further pushing said syringe plunger in said outer barrel of the syringe so as to discharge said liquid sample into said analyzer chamber.

* * * * *

UNITED STATES PATENT AND TRADEMARK OFFICE
CERTIFICATE OF CORRECTION

PATENT NO. : 4,256,461

DATED : March 17, 1981

INVENTOR(S) : William D. Wallace, Christopher A. Cutler, Justin S. Clark and Frederick L. Farr It is certified that error appears in the above-identified patent and that said Letters Patent are hereby corrected as shown below:

Column 4, line 30, "gap" should read -- cap --
line 65, "a" should read -- are --
Column 9, lines 2 - 3, cancel "deteriorating air contamination, the method comprising the steps of"

Signed and Sealed this

Twenty-third Day of June 1981

[SEAL]

Attest:

RENE D. TEGTMEYER

Attesting Officer     Acting Commissioner of Patents and Trademarks